(12) United States Patent
Lin

(10) Patent No.: US 7,637,878 B2
(45) Date of Patent: Dec. 29, 2009

(54) MULTI-FUNCTIONAL EYE MASSAGING DEVICE HAVING EXPANDABLE BODY

(76) Inventor: Pin-Hung Lin, 5F., No. 22, Wu Fen Street, Neihu District, Taipei City (TW)

(*) Notice: Subject to any disclaimer, the term of this patent is extended or adjusted under 35 U.S.C. 154(b) by 682 days.

(21) Appl. No.: 11/361,978

(22) Filed: Feb. 27, 2006

(65) Prior Publication Data
US 2006/0200052 A1    Sep. 7, 2006

(30) Foreign Application Priority Data
Mar. 4, 2005    (TW) .............................. 94106605 A (51) Int. Cl.
*A61H 1/00* (2006.01)
(52) U.S. Cl. ......................................... 601/70; 601/37
(58) Field of Classification Search .............. 601/37, 601/70, 71, 67; 607/109, 141
See application file for complete search history.

(56) References Cited
U.S. PATENT DOCUMENTS 6,155,995 A * 12/2000 Lin .............................. 601/15
7,158,834 B2 * 1/2007 Paul, Jr. ....................... 607/48
2005/0256433 A1 * 11/2005 Lin .............................. 601/70
2006/0135890 A1 * 6/2006 Tsai ............................. 601/15

* cited by examiner

Primary Examiner—Steven O Douglas
(74) Attorney, Agent, or Firm—Leong C. Lei (57) ABSTRACT

The eye massaging device contains a main member having built-in air pump and actuation elements, an inflatable fomentation member, and a belt member where the main member and the fomentation member are attached, and a controller for adjusting the settings of the massaging device. The main member contains a number of slidably engaged pieces that elastically expand along with the belt member when the device is tied around a user's head. Additionally, the eye massaging device can also provide simultaneous massages to the appropriate acupuncture spots at the sides of the head such as temples by having additional built-in vibrating elements.

10 Claims, 10 Drawing Sheets

MULTI-FUNCTIONAL EYE MASSAGING DEVICE HAVING EXPANDABLE BODY

BACKGROUND OF THE INVENTION (a) Technical Field of the Invention

The present invention generally relates to eye massaging devices, and more particularly to an eye massaging device capable of providing multiple massaging functions and whose body is expandable in accordance with a user's particular head size.

(b) Description of the Prior Art

A high percentage of urban school children suffer poor eyesight, especially myopia, resulted from prolonged period of eye usage with too much short-distance reading and viewing of books and TV programs.

Myopia can actually be corrected in the early stage with proper treatment. Together with people's awareness of the health of their eyes, therefore, quite a few eye care products using various techniques to release the pressure and tension of eye muscles have been available in the market.

Two such eye care products are disclosed by the present inventor as R.O.C. (Taiwan) Patent Nos. 169,241 and 195,314. A common drawback of the two teachings lies in that both their eye massaging devices cannot be flexibly expanded to properly cover the eyes of a user having a particular head size. As can be imagined, every person has his or her specific facial and head characteristics. Without the flexible expansion, the eye massaging device is inevitably displaced from its optimal location to provide the best massaging effect. On the other hand, these devices can only provide massage to the front of the user's head, but not to the important acupuncture spots at the sides of the head such as temples.

SUMMARY OF THE INVENTION

The primary purpose of the present invention is to an eye massaging device is provided herein whose massaging effect is not sacrificed when worn by a user with a particular head size by allowing its main member to expand or retract along the curvature of the user's head. The eye massaging device contains a main member having built-in air pump and actuation elements, an inflatable fomentation member, and a belt member where the main member and the fomentation member are attached, and a controller for adjusting the settings of the massaging device. The main member contains a number of slidably engaged pieces that elastically expand along with the belt member when the device is tied around a user's head. As such, the fomentation member and the actuation elements are positioned correctly at their optimal locations to provide a superior massaging effect.

An additional purpose of the present invention is that the eye massaging device can also provide simultaneous massages to the appropriate acupuncture spots at the sides of the head such as temples by having additional built-in vibrating elements.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following description are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
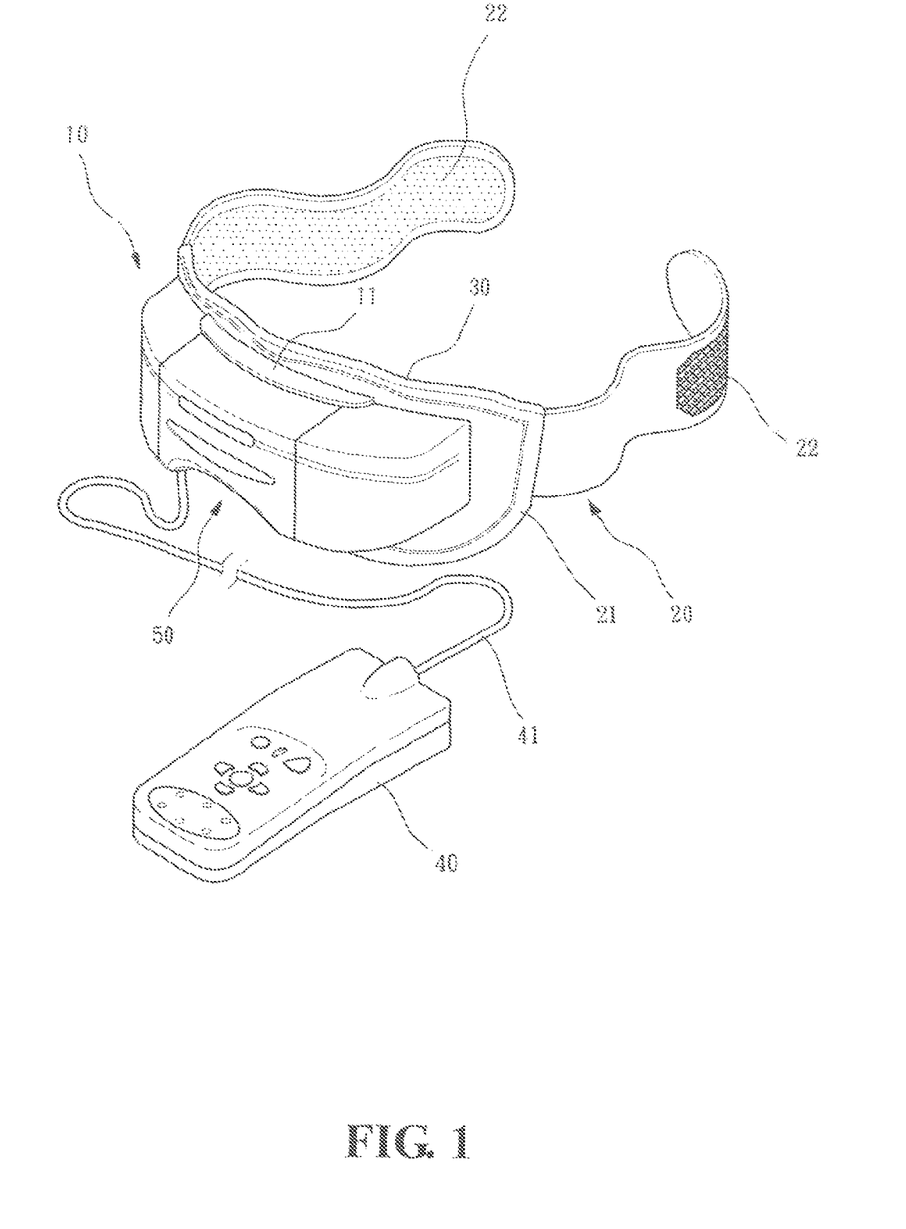
FIG. 1 is a perspective diagram showing the massaging device according to an embodiment of the present invention.
Figure 2:
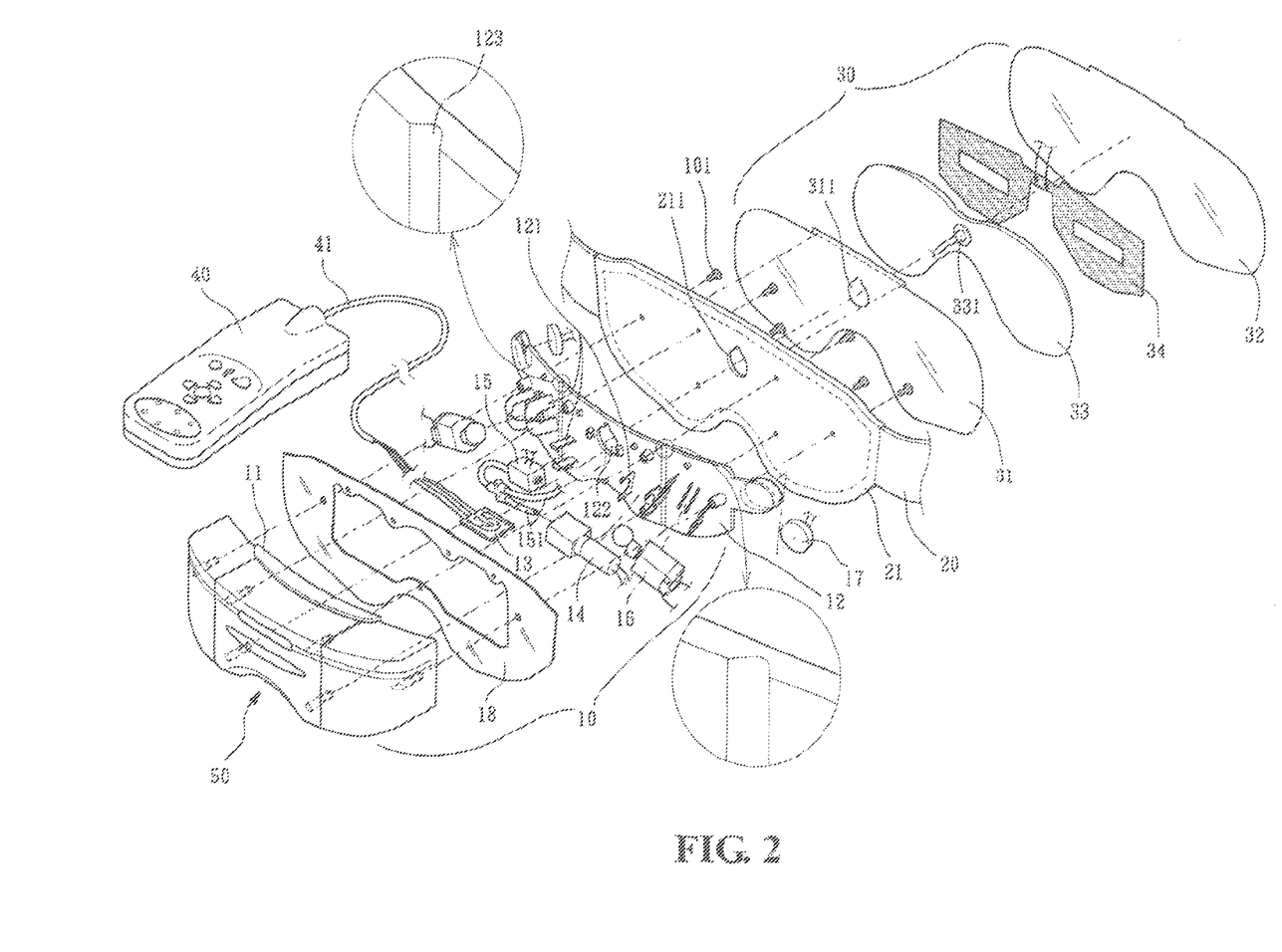
FIG. 2 is a perspective exploded diagram showing the various components of the massaging device of FIG. 1.

As illustrated in FIGS. 1 and 2, and embodiment of the present invention contains a main member 10 having built-in air pump and actuation elements and a fomentation member 30 capable of providing hot compress. The main member 10 and the fomentation member 30 are oppositely attached to the two sides of a belt member 20.

A supporting plate 21 is provided at an appropriate section along the belt member 20 for the attachment of the fomentation member 30 and the main member 10 from the two sides of the supporting plate 21 respectively. The belt member 20 has an appropriate elasticity and fastening elements 22 such as Velcro fasteners at the two ends. As such, the belt member 20 can be worn around a user's head so as to position the main member 10 and the fomentation member 30 on the user's eyes with an adjustable tightness appropriate to the user's comfort. Please note that all directional and positional references of the specification are made relatively to the user wearing an embodiment of the present invention.

The main member 10 mainly contains a hollow cover element 50 with an open side facing towards a base plate 12, and the two are jointly fixed to the front side of the supporting plate 21 by a number of bolt elements 101. Additionally, a washer plate 18 can be positioned between the cover element 50 and the base plate 12 and bolted to the supporting plate 21 altogether. The washer plate 18 can cover the base plate 12 for an enhanced appearance of the present embodiment. Masking pieces 11 are provided on the top and bottom rims of the cover element 50 respectively also for an enhanced appearance of the present embodiment. A viewing window is provided on the front surface of the cover element 50 so as to reveal the components housed inside the cover element 50 such as the indicator lamps. A number of seats 121 of various styles are provided on the front surface of the base plate 12 for the installation of a circuit board 13, and air pump 14, a leakage valve 15, and a number of actuation elements 16. The air pump 14 and the leakage valve 15 are for inflating and deflating the fomentation member 30. As such, a first air pipe 151 is connected between the air pump 14 and the leakage valve 15 which in turn connects to the fomentation member 30 via a second air pipe 151 threading through a hole 122 on the base plate 12. The actuation elements 16 generate vibrations with a massaging effect similar to the acupressure. The foregoing electrical components are all electrically connected to the circuit board 13. A number of longitudinal grooves 123 are provided on the front surface of the base plate 12 so that the base plate 12 can be curved appropriately, making the fomentation member 30 and the main member 10 closely attached to the eyes of the user having specific facial and head characteristics. Two vibrating elements 17 (e.g., thin vibrating motors) positioned on the two lateral ends of the base plate 12 have bulging portions right against the user's temples.

The fomentation member 30 has the shape of an eyeshade formed by a first outer piece 31 and a second outer piece 32, both made of, for example, fibers of bamboo charcoal capable of deodorization, ventilation, and providing negative ions and far infrared, or other far-infrared or nanometer materials, for enhancing the blood circulation of the eyes. An air bag 33 and a thin heating element 34 are enclosed by the two outer pieces 31 and 32 for providing hot compresses to the eyes. A faucet 331 is provided on the front surface of the air bag 33 which is connected to the second air pipe 151 threading through a hole 311 on the first outer piece 31 and the hole 211 of the supporting plate 21. The heating element 34 is electrically connected to the circuit board 13 via the same route and is heated by the electricity provided from the circuit board 13. As such, the air pump 14 and the leakage valve 15 can inflate and deflate the air bag 13 to press the warm heating element 34 against the eyes with various levels of pressure.

An ergonomically designed handheld controller 40 is connected to the circuit board 13 via a cable 41. Various control buttons and adjustment knobs are provided on the surface of the controller 40 so as to control the inflation of the air bag 33, the vibration strength of the actuation elements 16, the temperature of the heating element 34, etc., or some fully automated massaging processes involving the foregoing parameters.

Figure 3:
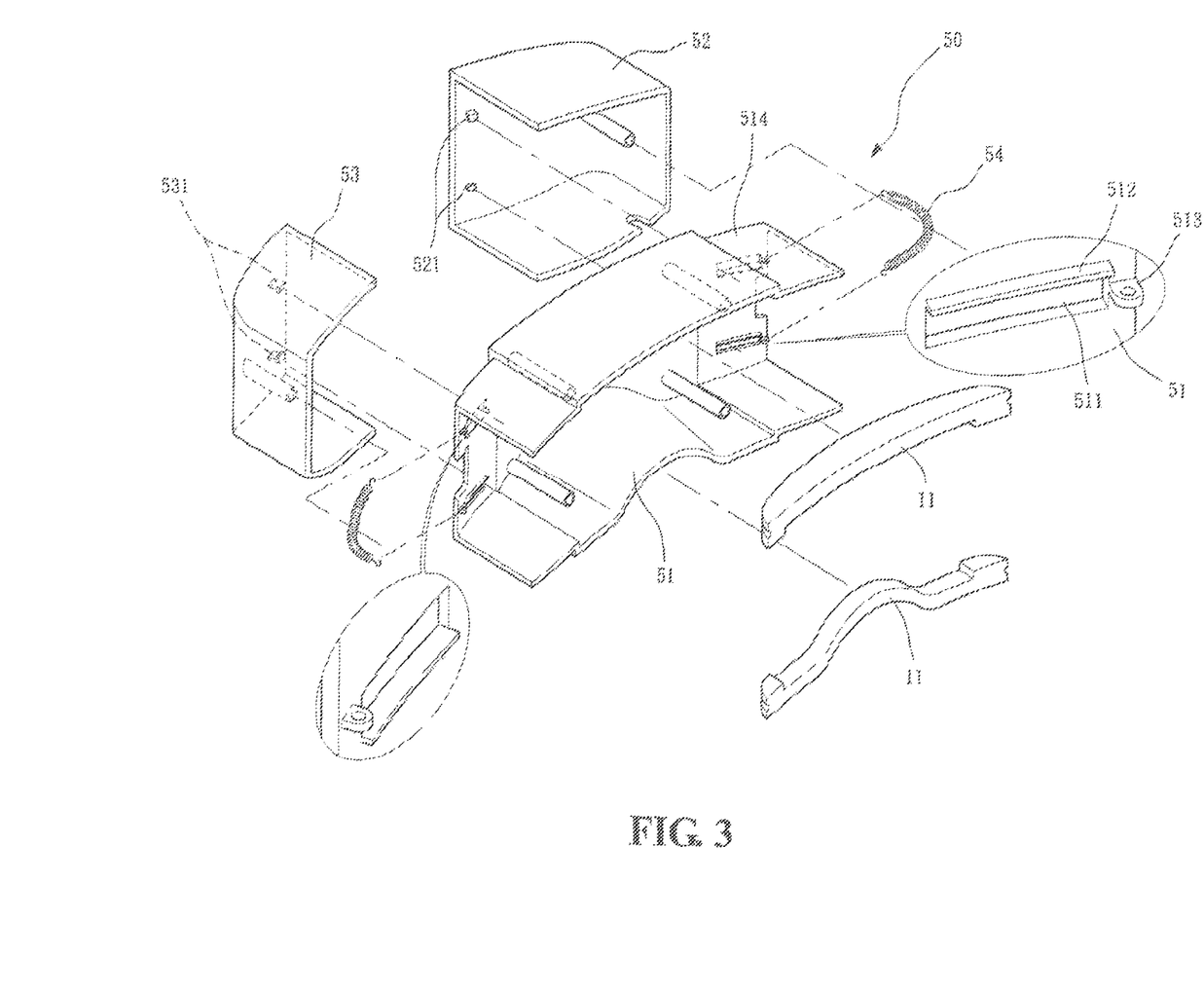
FIG. 3 is a perspective exploded diagram showing the cover element according to a first embodiment of the present invention.
Figure 4:
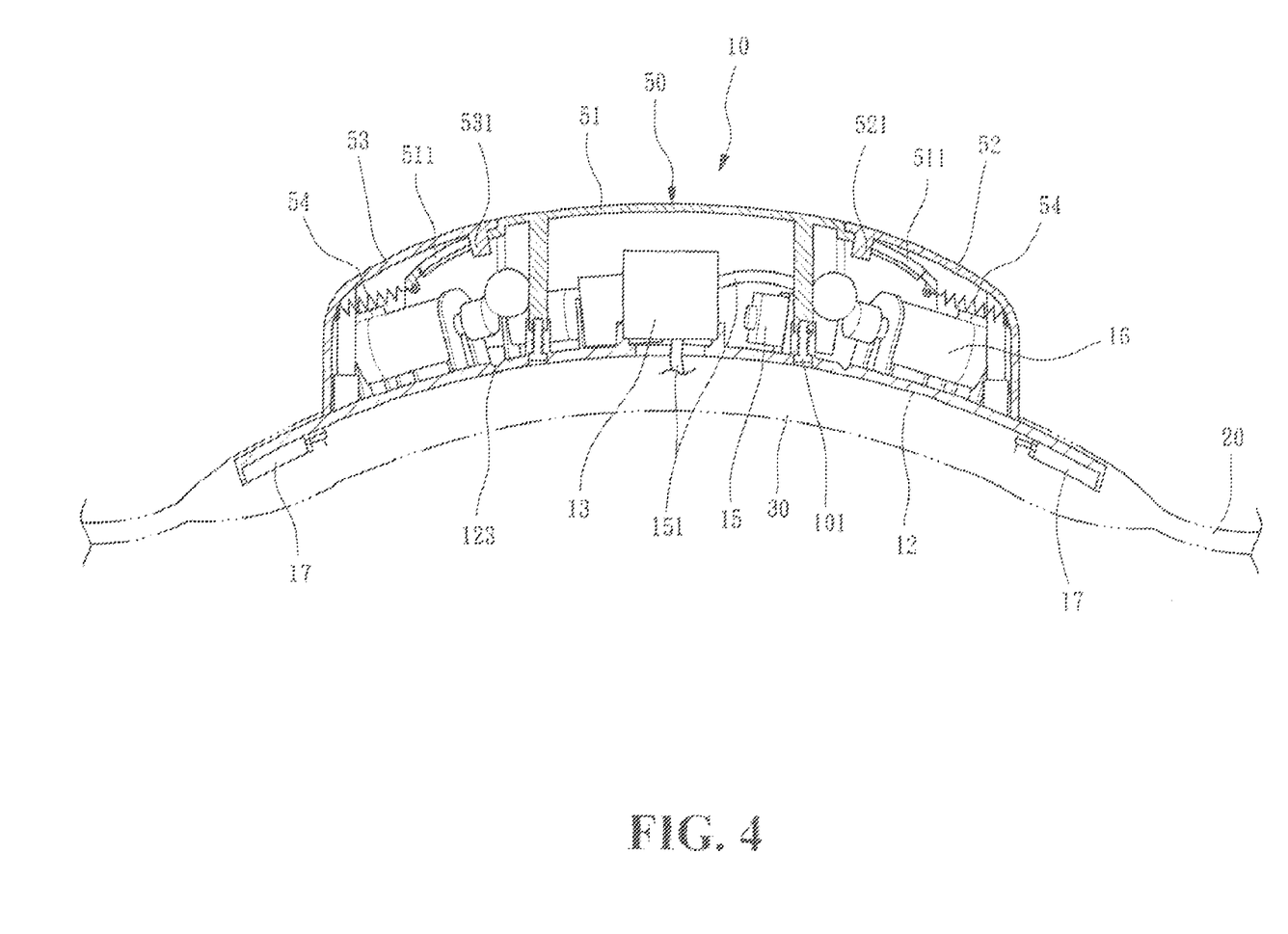
FIG. 4 is a schematic cross-sectional diagram showing the cover element of FIG. 3.

As shown in FIGS. 3 and 4, the cover element 50 contains a U-shaped first piece 51 whose trough opens to the base plate 12. The width of the trough is slightly smaller at the two lateral end portions 514 which are housed inside a second piece 52 and a third piece 53 respectively. On the front side of each lateral end portion 514, two lateral slots 511 are provided substantially in parallel. Along a lateral edge of each lateral slot 511, a flange 512 is provided protruding towards the inside of the first piece 51. Two ends of a helix spring 54 are fixedly connected two ears 513 adjacent to the outer ends of the slots 511 within the same lateral end portion 514. The second and third pieces 52 and 53 have two L-shaped hooks 521 and 531 on their inner surfaces respectively that can penetrate through the slots 511. The longitudinal portion of the L-shaped hooks 521 and 531 are blocked by the flanges 512 so that the second and third pieces 52 and 53 are slidably engaged with the lateral end portions 514 of the first piece 51 without falling off. As such, the second and third pieces 52 and 53 can be expanded to the two lateral sides of the first piece 51 with the L-shaped hooks 521 and 531 sliding within the slots 511. Please note that the middle portions of the helix springs 54 are attached a structural element (e.g., a protruding stick in the present embodiment) on the inner surface of the second and third pieces 52 and 53 respectively. Therefore, when the second and third pieces 52 and 53 expand, they are under a resilient force by the helix springs 54 to return them back to their original positions.

Figure 5:
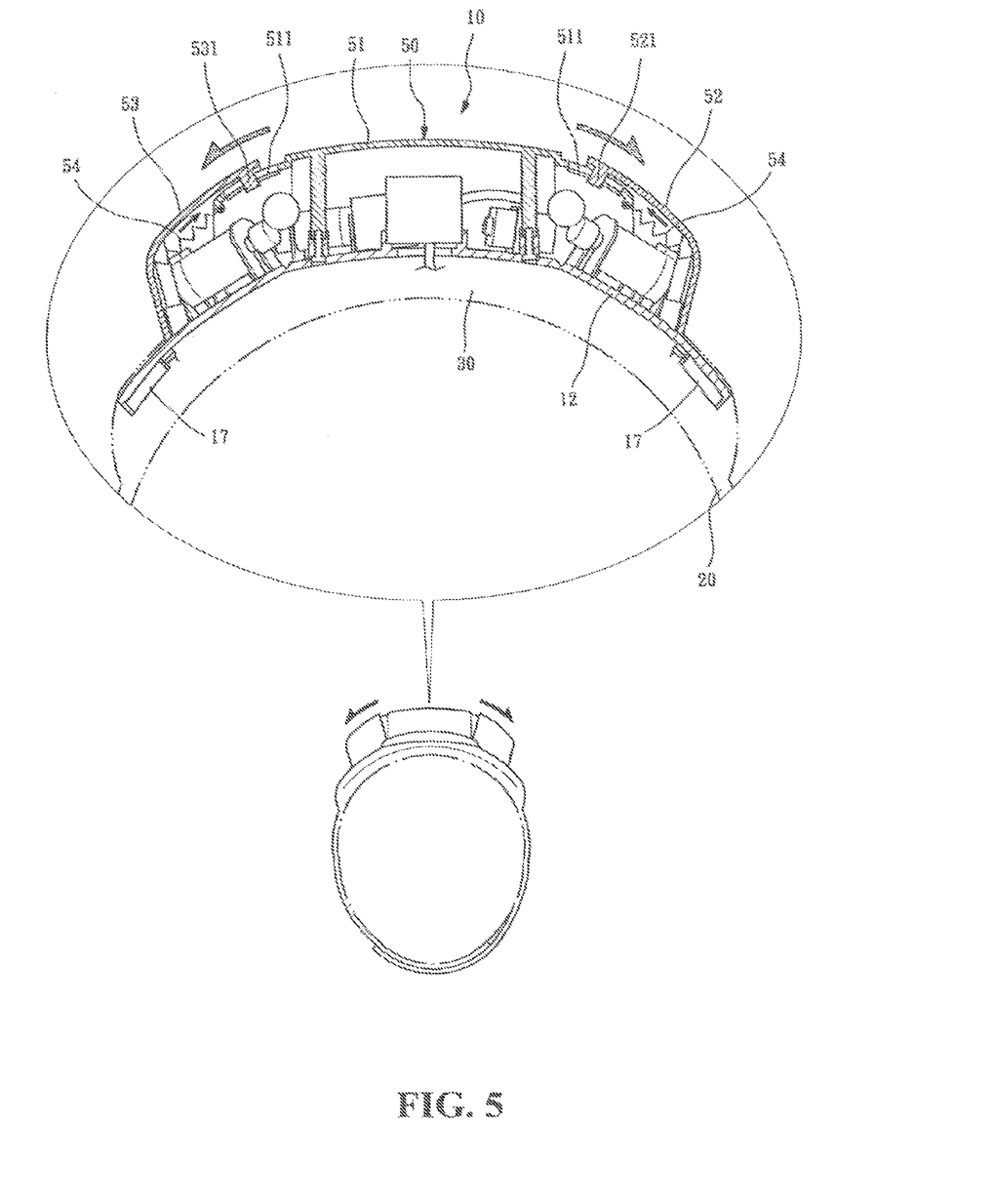
FIG. 5 is a schematic cross-sectional diagram showing the cover element on a user having a larger head size.
Figure 6:
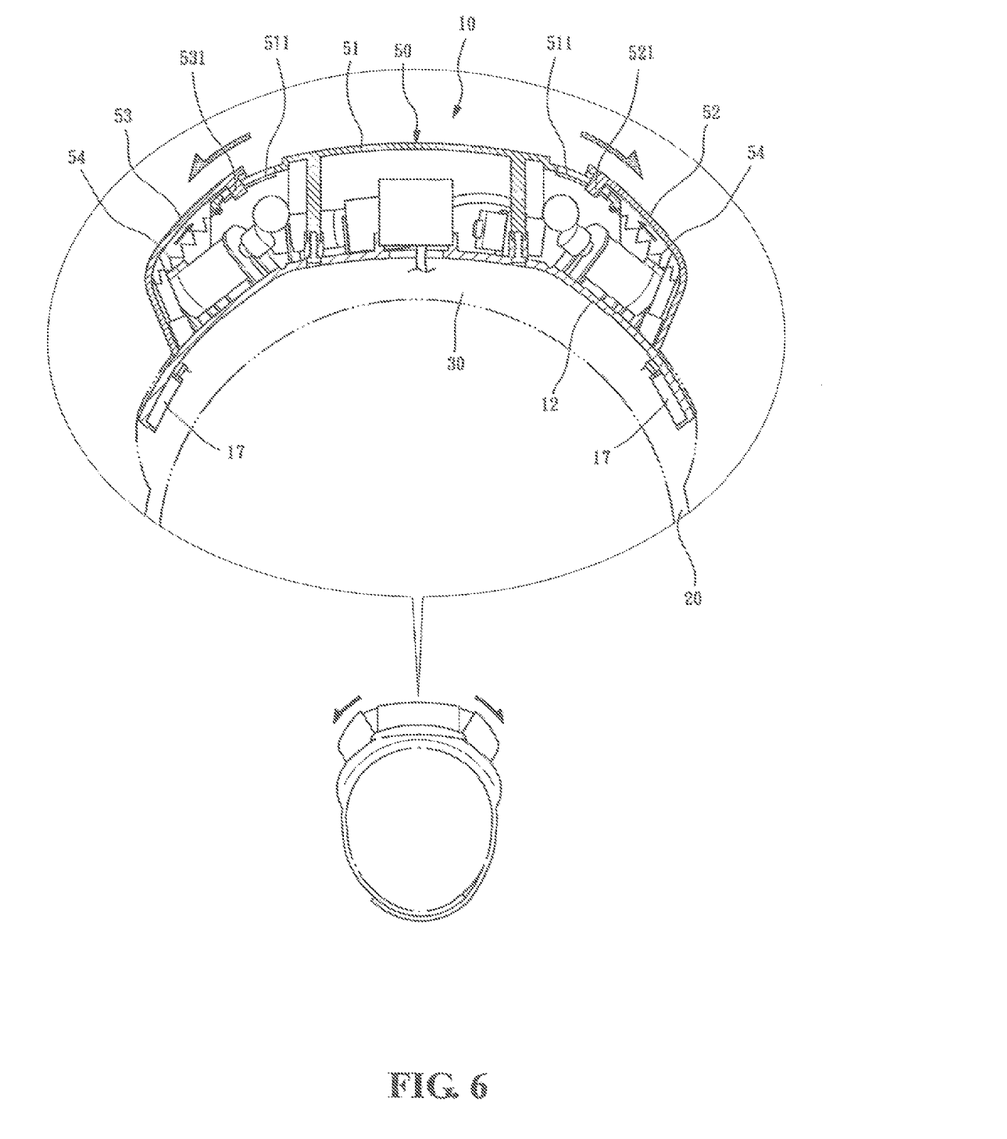
FIG. 6 is a schematic cross-sectional diagram showing the cover element on a user having a smaller head size.

As shown in FIGS. 5 and 6, when the present embodiment is worn on a grown-up with a larger head size or a children with a smaller head size by the belt member 20, the second and third pieces 52 and 53 of the cover element 50 will expand or retract in accordance with the curvature of the user's head so that the present embodiment can be perfectly matched against the head of a particular user.

Figure 7:
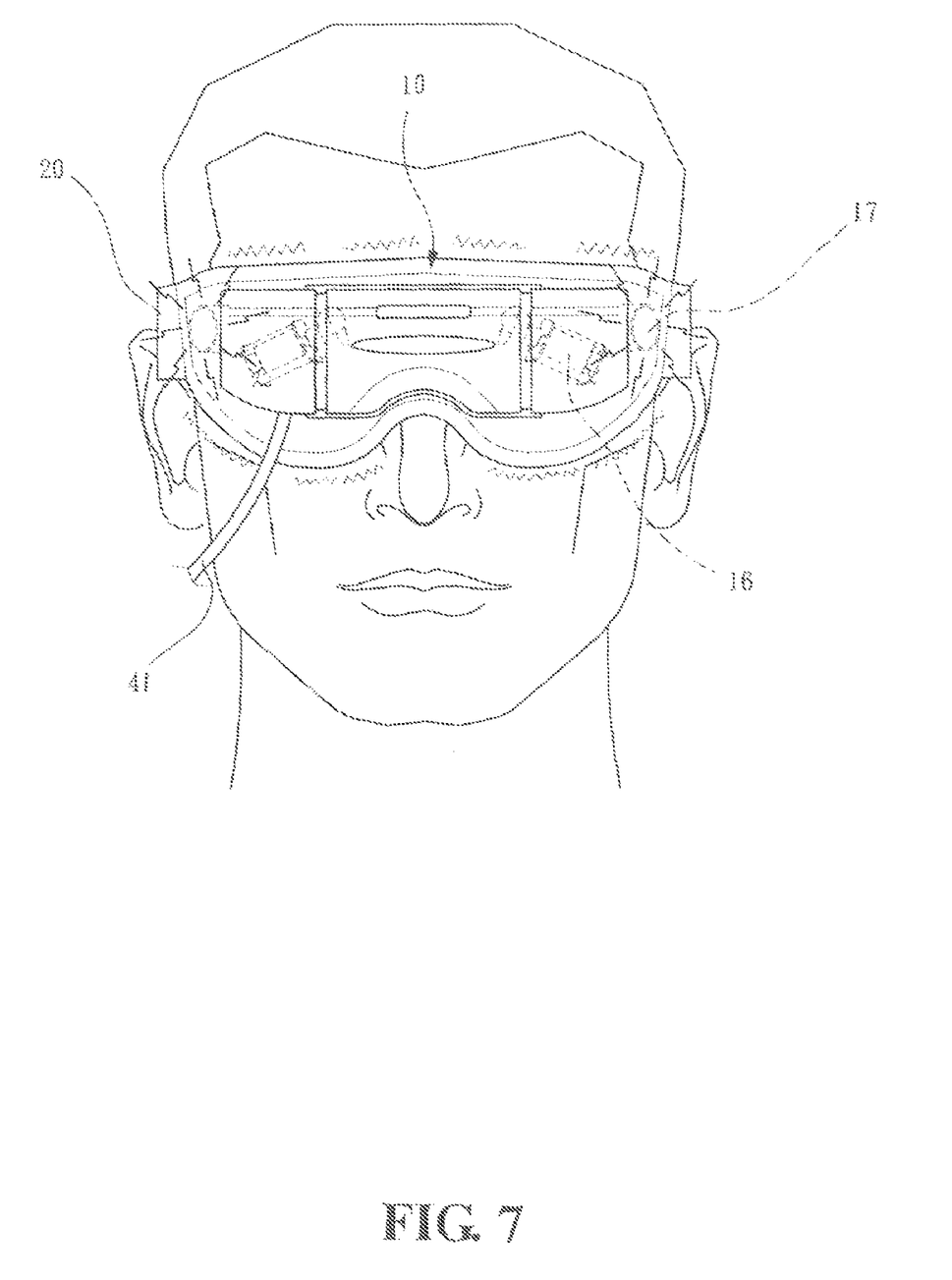
FIG. 7 is a schematic front diagram showing the application of the massaging device of FIG. 1.
Figure 8:
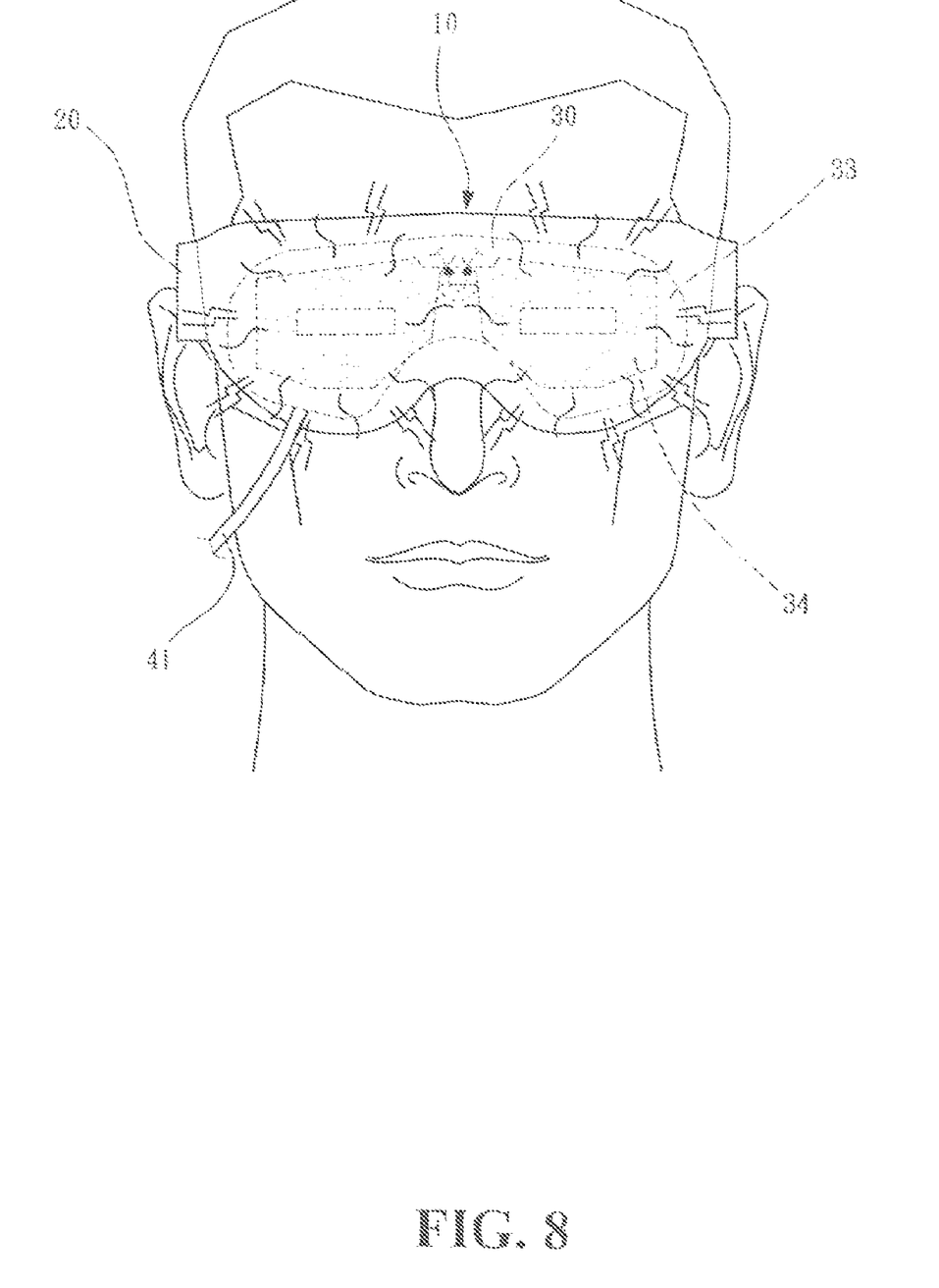
FIG. 8 is another schematic front diagram showing the application of the massaging device of FIG. 1.

As shown in FIGS. 7 and 8, the present embodiment covers the user's eyes like an eyeshade. By the control function of the controller 40, the air bag 33 and the heating element 34 can have a desired pressure level and temperature in accordance with a user's preference. The air bag 33 can be inflated and deflated periodically so as to provide a massaging effect similar to performing acupressure by fingers. In addition, the vibrating elements 17 can deliver vibrations to the user's temples for releasing the user's pressure.

Figure 9:
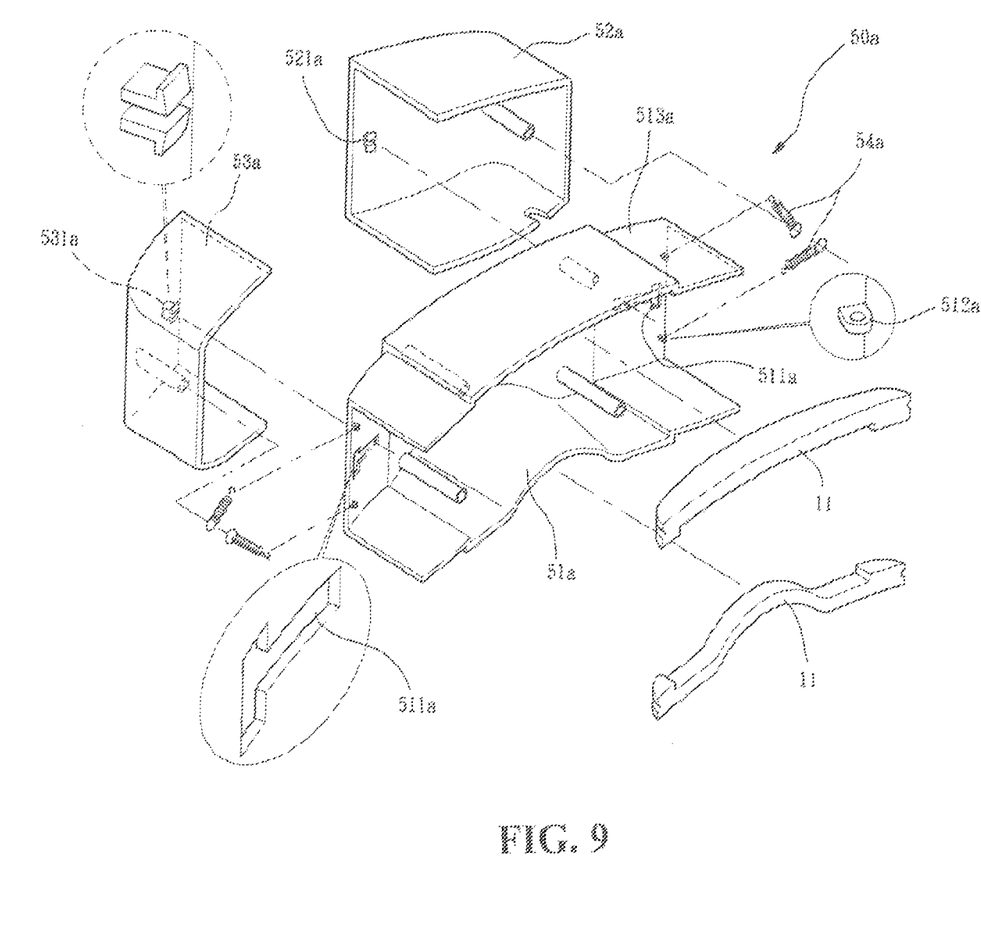
FIG. 9 is a perspective diagram showing the cover element according to a second embodiment of the present invention.

FIG. 9 is a perspective diagram showing the cover element according to a second embodiment of the present invention. As illustrated, the cover element 50a contains a U-shaped first piece 51a whose trough opens to the base plate 12. The width of the trough is slightly smaller at the two lateral end portions 513a which are housed inside a second piece 52a and a third piece 53a respectively. On the front side of each lateral end portion 513a, a 90-degree-turned T-shaped lateral slot 511a is provided. The second and third pieces 52a and 53a have hooks 521a and 531a respectively that can penetrate through the slots 511a. Each of the hooks 521a and 531a contains two L-shaped elements sitting back to back with their longitudinal portions blocked by the lateral banks of the slot 511a so that the second and third pieces 52a and 53a are slidably engaged with the lateral end portions 513a of the first piece 51a without falling off. Two ears 512a are provided above and below each slot 511 respectively in each lateral end portion 513a. Two helix springs 54a have one of their ends fixedly connected to the two ears 512a respectively within the same lateral end portion 51a. The other ends of the helix springs 54a are jointly connected to a structural element (e.g., a protruding stick in the present embodiment) on the inner surface of the second and third pieces 52a and 53a respectively. Therefore, when the second and third pieces 52a and 53a expand, they are under a resilient force by the helix springs 54a to return them back to their original positions.

Figure 10:
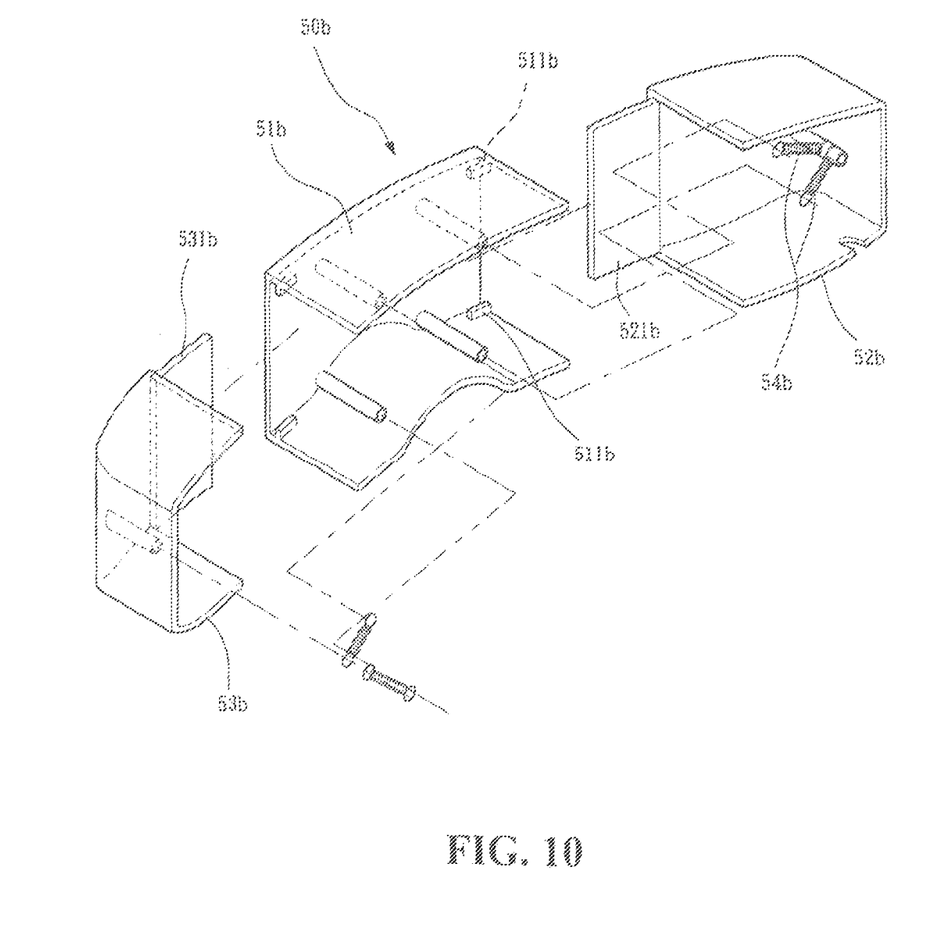
FIG. 10 is a perspective diagram showing the cover element according to a third embodiment of the present invention.

FIG. 10 is a perspective diagram showing the cover element according to a third embodiment of the present invention. As illustrated, the cover element 50b contains a U-shaped first piece 51b whose trough opens to the base plate 12. At each of the two lateral ends of the first piece 51b, a pair of longitudinally expanded blocks 511b are provided from the upper and lower inner surface of the first piece 51b respectively. On the other hand, the second and third pieces 52b and 53b have laterally expanded guiding plates 521b and 531b respectively. By having the guiding plates 521b and 531b confined by the blocks 511b, the second and third pieces 52b and 53b are slidably engaged with the first piece 51b at its two lateral ends respectively. For each of the second and third pieces 52b and 53b, two helix springs 54b have one of their ends fixedly connected to two structural elements (e.g., two protruding sticks in the present embodiment) on the inner surface of the first piece 51b. The other ends of the helix springs 54a are jointly connected to a structural element (e.g., a protruding stick in the present embodiment) on the inner surface of the second and third pieces 52b and 53b respectively. Therefore, when the second and third pieces 52b and 53b expand, they are under a resilient force by the helix springs 54b to return them back to their original positions.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An eye massaging device, comprising:
a belt member for wearing on a user's head; and
a main member attached to a front side of said belt member covering a user's eyes, said main member having built-in active components delivering massaging functions, wherein said main member has a base plate and a U-shaped cover element having a trough which opens to said base plate joined to a front of said base plate; said cover element has a first piece, a second piece, and a third piece; two lateral end portions of said first piece are housed inside said second and third pieces respectively; at least a lateral slot is provided on a front side of each of said lateral end portions, each of said second and third pieces has at least a hook on an inner surface that penetrates through and locks to said slot so that said second and third pieces are slidably engaged with said lateral end portions of said first piece.

2. The eye massaging device according to claim 1, wherein a flange protruding towards an inside of said first piece is provided along a lateral edge of each said lateral slot; and each said hook has an L-shape whose longitudinal portion locks to said flange of said lateral slot.

3. The eye massaging device according to claim 2, wherein each said lateral slot has a 90-degree-turned-T shape; each said hook has two L-shaped elements positioned back to back with the longitudinal portion which locks to lateral banks of said lateral slot.

4. The eye massaging device according to claim 1, wherein at least a first elastic element engages said first piece and said second piece; at least a second elastic element engages said first piece and said third piece; when said second and third pieces are slid relatively to said first piece, said first and second elastic elements provide resilient force in opposite direction.

5. The eye massaging device according to claim 1, wherein a plurality of longitudinal grooves are provided on a front surface of said base plate allowing said base plate to curve appropriately.

6. The eye massaging device according to claim 1, wherein a vibrating element is provided on each of the lateral ends of said base plate corresponding to a user's temples.

7. The eye massaging device according to claim 1, wherein a plurality of seats are provided on a front surface of said base plate where said active components are fixedly positioned.

8. The eye massaging device according to claim 1, wherein two masking pieces are provided along top and bottom rims of said cover element respectively.

9. The eye massaging device according to claim 1, further comprising a fomentation member attached to the other side of said belt member opposite to said main member.

10. The eye massaging device according to claim 9, wherein an outer cover of said fomentation member is made by one of the materials: fiber of bamboo charcoal, far-infrared material, and nanometer material.

* * * * *